United States Patent [19]
Davies et al.

[11] Patent Number: 4,905,707
[45] Date of Patent: Mar. 6, 1990

[54] METHOD FOR RECOGNIZING REJECTION OF TRANSPLANTED HEARTS

[75] Inventors: David W. Davies, London, England; Bengt A. Lekholm, Bromma, Sweden

[73] Assignee: Siemens Aktiengesellschaft, Berlin and Munich, Fed. Rep. of Germany

[21] Appl. No.: 939,343

[22] Filed: Dec. 8, 1986

[51] Int. Cl.[4] .............................................. A61B 5/04
[52] U.S. Cl. .................................................... 128/702
[58] Field of Search ................................ 128/702–705

[56] References Cited

U.S. PATENT DOCUMENTS

| 3,593,705 | 7/1971 | Thomas et al. | 128/703 |
| 3,707,959 | 1/1973 | Wilton-Davies | 128/703 |
| 4,336,810 | 6/1982 | Anderson et al. | 128/702 |
| 4,360,030 | 11/1982 | Citron et al. | 128/702 |
| 4,679,144 | 7/1987 | Cox et al. | 128/705 |

Primary Examiner—William E. Kamm
Attorney, Agent, or Firm—Hill, Van Santen, Steadman & Simpson

[57] ABSTRACT

A method is disclosed for monitoring the body reaction against a heart transplant. When a heart is newly transplanted, electrocardiac signals from the transplanted heart are detected. The analog signals are converted to digital signals. A first differentiation of the digital signals is carried out over a continuous time period to create reference differentiated signals. At a later time during monitoring of the transplanted heart, analog electrocardiac signals are again detected from the transplanted heart. These analog signals are converted to digital signals. A first differentiation is carried out of these digital signals over a continuous time period to create monitored differentiated signals. The reference differentiated signals and the monitored differentiated signals are compared at least with respect to amplitude to create comparison results. All of the above operations occur within the body. These comparison results are recorded and stored for use in determining body rejection of the transplanted heart.

12 Claims, 3 Drawing Sheets

FIG. 1
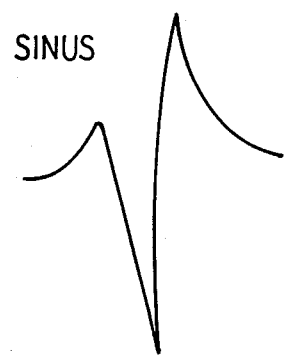
FIG. 2
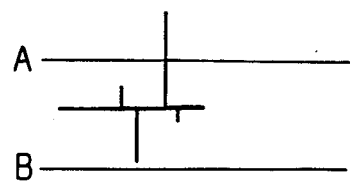
RAE
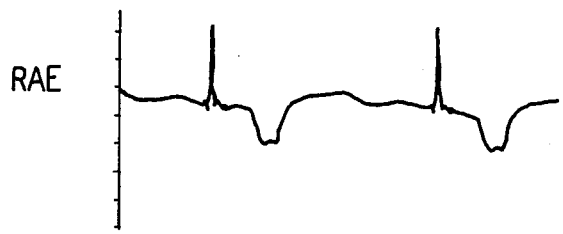
FIG. 3
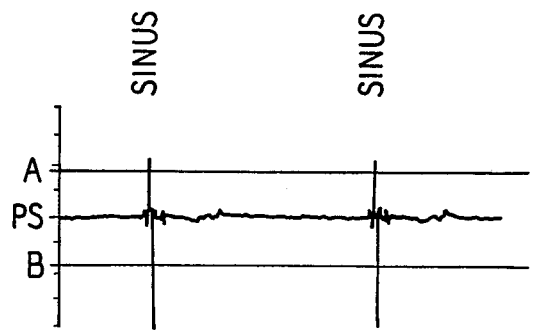
FIG. 4

METHOD FOR RECOGNIZING REJECTION OF TRANSPLANTED HEARTS

BACKGROUND OF THE INVENTION

This invention relates to a method for recognizing rejection of transplanted hearts. The invention relates in particular, but not exclusively; to cardiac implants for detecting and alerting a patient to rejection of a transplanted heart.

After a human heart transplantation, it is necessary to monitor the recipient's body reaction against the implanted heart to prevent destruction of the new heart by an immune reaction. Commonly employed methods for detecting rejection are cumbersome and invasive. It is known that the morphology of cardiac electrograms alters during a rejection process, although this observation has not hitherto found practical use. For practical reasons, the preferred method of monitoring the cardiac electrogram would be by use of an implanted pacemaker which would be able to transmit the electrogram via telemetry to an external device such as a tape recorder or a paper recorder. The main limitation of this method lies in the poor transmission properties of the pacemaker electrocardiogram amplifier and the weakness of the telemetry link to the outside world.

More specifically, current pacemaker sensing amplifiers are relatively unsophisticated in the detection of intracardiac signals, relying entirely upon simple amplitude and frequency band pass filtration analysis.

For technical reasons, it is difficult to improve on the transmission properties of the electrogram of a pacemaker. Thus, the extraction of information about changes in the electrogram must be done inside the pacemaker before transmission to the external equipment takes place. To do this efficiently in an implantable system is only possible if there exists a simple and powerful algorithm by which relevant information about the signal morphology can be obtained.

SUMMARY OF THE INVENTION

It is an object of this invention to disclose a method for monitoring the body reaction against a transplanted heart to allow timely measures to be taken against rejection.

According to the present invention, a method is disclosed for monitoring the body reaction against a heart transplant.

When a heart is newly transpslanted, electrocardiac signals from the transplanted heart are detected. The analog signals are converted to digital signals. A first differentiation of the digital signals is carried out over a continuous time period to create reference differentiated signals. At a later time during monitoring of the transplanted heart, analog electrocardiac signals are again detected from the transplanted heart. These analog signals are converted to digital signals. A first differentiation is carried out of these digital signals over a continuous time period to create monitored differentiated signals. The reference differentiated signals and the monitored differentiated signals are compared at least with respect to amplitude to create comparison results. All of the above operations occur within the body. These comparison results are recorded and stored for use in determining body rejection of the transplanted heart.

The present invention thus encompasses both cardiac implants modified to embody this invention either (A) to be worn by a patient discharged from a hospital and/or (B) to be worn by a patient who is in a postoperative phase within a hospital. A method embodying this invention is superior to that previously proposed in that, since the data reduction has been done inside the pacemaker, the requirements on a telemetry link are greatly relieved so that this operation no longer is limited by the quality of the telemetry link. Moreover, insofar as use by a patient is outside a hospital, he may be warned by an audible signal when the implanted pacemaker is transmitting signals suggesting rejection of the heart. The patient will then be able to consult his physician who, by obtaining transmission of stored data, will be able to obtain the comparison of differentiated signals in readable form and can establish the extent of rejection which is taking place. Infusion of a rejection suppressing drug can then be prescribed for the patient. At a future time it is envisaged that an in board pump for supply to the body of such a drug might be activated. Alternatively, if the indications are spurious, then this would mean at least that the implant is malfunctioning and should be replaced, repaired, or reprogrammed.

The concept of gradient pattern detection (GPD) in clinical electrophysiology utilized in the method of this invention is a recent one described, for example, in the portion of U.S. Ser. No. 100,722 to Davies entitled "Apparatus For Recognizing Cardiac Rhythms" which is common to abandoned Ser. No. 793,538, describing specifically the detection of and response to cardiac arrhythmias, and incorporated herein by reference. However, it could not have been appreciated from U.S. Ser. No. 100,722 that the principle thereof would prove of particular benefit for checking for signs of rejection of implanted hearts using telemetry.

In contrast to other methods of analysis of the morphology of intracardiac electrograms, the method of the present invention utilizes the principle of gradient pattern detection. This is a simpler algorithm requiring less in the way of computing power, and does not reduce implant battery life to the same extent as other methods, such as fast Fourier transformation and template matching. Although gradient pattern detection (GPD) consumes battery power additional to that consumed when detection of heart implant rejection is carried out using conventional methods, it is not necessary to operate continuously the apparatus embodying this invention. GPD will only need to be effected at predetermined intervals since rejection does not occur instantaneously, but over a period of time.

Satisfactory performance of the method of this invention is dependent on the stability of the sensing electrode, as even small movements of the electrode tip would be expected to produce unpredicted differences in electrogram shape. In experiments, recordings obtained using temporary electrodes with conventional "passive" tips yielded stable electrogram morphology within each rhythm despite this movement and the postural and the respiratory variations encountered.

The principle behind the method of this invention will now be described in greater detail with reference to sinus rhythm, that is the normal rhythm of a heart in stable fashion. Thus, in a first step, electrograms are sensed in the usual manner shortly after implantation of the replacement heart, sensing generally taking place at a signal frequency in the range of 0.016 Hz–1 kHz, with a preferred range between from 0.5 Hz to 500 Hz, the electrograms being obtained during sinus rhythm. The analog electrograms produced are then converted to digital form preferably using an analog-to-digital converted frequency of 1024 Hz. The digital electrograms are then converted to a first differential form where the amplitudes of this processed signal are proportional to the gradients (slopes or slew-rates) of the original analog signal. The resultant sequence of amplitudes and their temporal spacing is then stored. Subsequently, during continued operation of the heart, electrograms are produced and processed in like manner and compared with the processed "normal" electrogram to determine whether changes have taken place which are symptomatic of development of heart rejection. This comparison will be sufficiently sensitive to show the small changes which take place indicating the onset of rejection. The electrograms will have, as a result of rejection, lower amplitude and slew rates. The method will be specific both to the patient and the location at which the sensors are placed.

Put at its simplest, this invention involves comparison of the first differentials of the slopes of the digital electrograms of each beat with what is established for the first differential of the slopes of the digital electrograms before rejection. As will be apparent from FIG. 2 of the accompanying drawings, each beat has gradients whose gradient differentials will differ from each other in magnitude, polarity and interval. It may be sufficient for many purposes to rely merely on gradients of and intervals between the processed signals being compared. A particularly sophisticated form of control can be achieved if scanning is carried out only at intervals, with it being necessary for a particular sequence of deflections of particular magnitude to be achieved within a particular time interval and generally in a particular order within that time interval, which parameters are, of course, established when the heart has been operating stably, that is the programmable window is utilized for comparison purposes.

BRIEF DESCRIPTION OF THE DRAWINGS

FIG. 1 is a schematic plot of amplitude versus time for successive beats of a patient showing normal beats;

FIG. 2 shows an approximate first derivative of the signals of FIG. 1;

FIG. 3 shows a copy of an experimentally obtained analogue electrogram;

FIG. 4 shows a copy of the derivatives of the electrogram;

DESCRIPTION OF THE PREFERRED EMBODIMENTS

Figure 5:
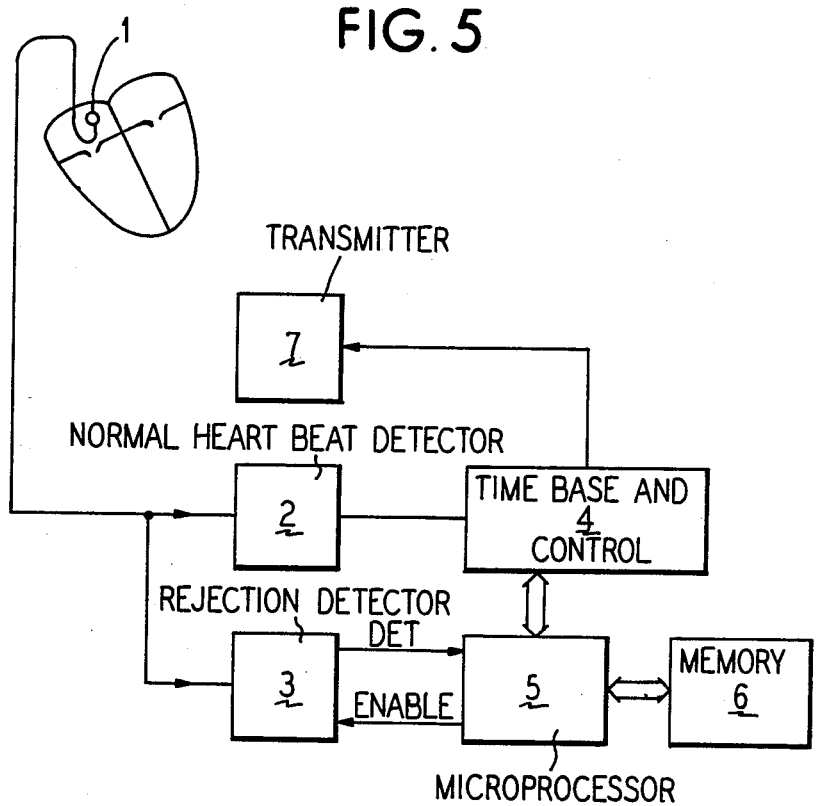
FIG. 5 is a block diagram of an embodiment of a embodying the method of the invention.

As can be seen from FIG. 1, each beat is shown to possess two peaks which differ in gradient and amplitude between the respective peaks, although there may be a different number of peaks. Insofar as FIG. 1 is concerned, there are four slopes to each beat and thus, referring to FIG. 2, the first differential of each slope will be correspondingly different as to magnitude, polarity and spacing from the other differentials associated with the beat. This derivative plot, through its simplicity, can yield useful indications and requires less power to transmit by telemetry, an advantage in view of the poor transmission properties of a pacemaker electrocardiogram amplifier and the weakness of telemetry links to the outside world. It will enable even small changes in heart performance to be detected.

An analog electrogram obtained in practice is shown in FIG. 3 of the drawings. FIG. 4 shows derivatives of the processed signals. The threshold lines A and B illustrate the mechanism. For recognition of a condition in which rejection is not taking place, line A followed by line B both have to be crossed by the process signal (PS). A failure of either line A or line B to be crossed by PS may denote rejection of the implanted heart. Such sensing coupled with change in separation between successive intersections will indicate deterioration.

In practical determinations to obtain results of the type shown in FIGS. 3 and 4 electrograms have been recorded from 1 cm bipoles in the atrium and either 1 cm bipoles or 0.5 cm bipoles at the right ventricular apex (RVA), a single surface ECG channel being recorded simultaneously. The intracardiac recordings were made either from DC to 1 kHz or from 0.016 Hz to 1 kHz using a Biodata P400 amplifier onto a Racal store 7 tape recorder. The analog electrograms recorded were then digitized at a sampling frequency of 1024 Hz. This relatively low sampling frequency was chosen first because the electrogram frequency spectrum contains little useful information among higher frequencies, and secondly with a view to implantability of a pacemaker embodying the invention and the need to consider battery conservation. The digital electrogram was then converted into a form closely resembling its first time derivative where the amplitudes of the derived signal were proportional to the rates of change of the original electrogram. The derived signal was then analyzed by a gradient pattern detection method which examined for the sequence of turning point and more particularly for the magnitude of amplitudes and the temporal separation within the derived signal. The values obtained were then compared with those within a reference signal obtained during sinus rhythm shortly after implanting of the heart, recognition of rejection being based upon the difference between the sequences. Such recognition occurs when certain individually adjustable criteria were met by the derived signal and terminated after an adjustable number of gradients within the signal had occurred. The triggering criteria consisted, for example, of deflections of the processed signal (of either polarity) being less than thresholds for amplitudes and these being sustained for a preset minimum number of sampling points. Satisfaction of these requirements ensures that extraneous "noise" was not misinterpreted. The sequence of gradients within the original electrogram was detected by analysis of the amplitudes of the subsequent deflections of the processed signals. Rejection of the heart was detected when the amplitudes of the deflections differed in magnitude from those seen before rejection particularly if coupled with changing intervals between equivalent deflections. Variations of respiration, posture and sinus rate have not been found to alter atrial electrogram morphology in patients in such a way as to affect recognition by GPD despite the fact that there may have been noticeable changes in analog electrogram amplitudes in patients. Moreover, similar types of results have been obtained when producing ventricular electrograms.

Figure 6:
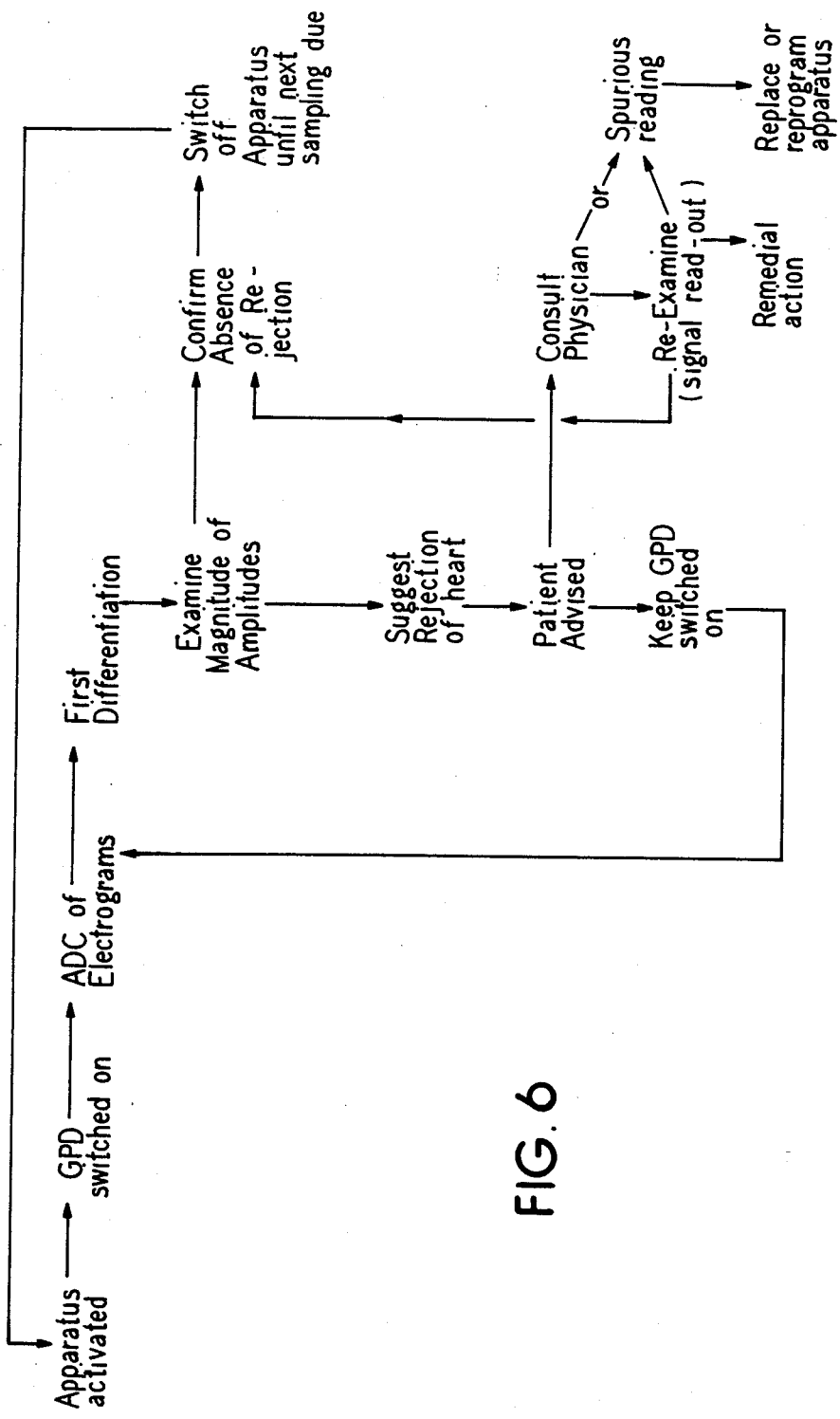
FIG. 6 is a flow diagram of the steps involved in recognizing rejection of a heart using the method of this invention.

Finally, FIGS. 5 and 6 show practical embodiments for performing the method of the invention and should be viewed in conjunction with each other.

Thus, an implant located at, for example, an atrial location may monitor heart rate at pre-programmed intervals using a normal heart beat detector 2 having time base and control 4 whose operation is directed by a microprocessor 5 having a memory 6. At such sampling intervals, gradient pattern detection is switched on at rejection detector 3 which is normally operating in back-up mode. Electrograms produced in detector 3 are subjected to an analog-to-digital conversion and the digitalized signals are subjected to a first differentiation. The amplitude and generally also sequence, interval, and polarity of the deflections of the processed signals obtained are examined. With the assistance of memory 6, these first differentials are compared with first derivative values characteristic of the rhythm before rejection. If there is a match, then no device for warning a patient will be actuated. However, if there is a variation indicating possible signs of heart rejection, then the variance will generally be manifested through a change in magnitude of the derived function as well as possibly changes in sequence, polarity, and interval, and a signal will be delivered from control 4 to transmitter 7. The purpose of the signal from transmitter 7 is to warn the patient to consult his physician. The transmitter 7 is provided with a storage memory and the physician can interrogate this memory to obtain retransmission of the original signals to means for reproducing the stored signals in a readable form. If the indications are of heart rejection, then the GPD may be switched on externally and further readings obtained. If the physician is satisfied that rejection is taking place, remedial action may be effected. However, if it is shown that the readings were spurious, either the GPD will be switched off or reprogrammed, or the GPD may be kept operating on a continuous basis for the purposes of examination. If it should be shown that there is malfunctioning, then surgery will be required to achieve replacement of components of the pacemaker.

Although various minor changes and modifications might be suggested by those skilled in the art, it will be understood that we wish to include within the claims of the patent warranted hereon all such changes and modifications as reasonably come within our contribution to the art.

We claim as our invention:

1. A method of monitoring a body reaction against a heart transplanted therein, comprising steps of:
   detecting inside the body analog electrocardiac signals from a newly transplanted heart in the body;
   within the body converting the analog signals to digital signals;
   within the body carrying out a first differentiation of the digital signals over a continuous time period to create reference differentiated signals;
   at a later time during monitoring of the heart, again detecting within the body analog electrocardiac signals from the transplanted heart;
   within the body converting the analog signals to digital signals;
   within the body carrying out a first differentiation of the digital signals over a continuous time period to create newly monitored differentiated signals;
   within the body comparing the newly monitored differentiated signals with the reference differentiated signals to create comparison results;
   recording and storing within the body the comparison results; and
   at a desired time, transmitting the stored comparison results from inside the body to outside the body for use in analyzing body rejection of the transplanted heart.

2. A method according to claim 1 wherein amplitudes of the reference and newly monitored differentiated signals are compared.

3. A method according to claim 1 wherein intervals of the reference and newly monitored differentiated signals are also compared.

4. A method according to claim 1 wherein polarities of the reference and newly monitored differentiated signals are compared.

5. A method according to claim 1 wherein an amplitude sequence of said reference and newly monitored differentiated signals are also compared.

6. A method according to claim 1 including an additional step of supplying said compared results on demand by telemetry from internally to externally of the body.

7. A method according to claim 6 including the step of altering a patient to an unfavorable assessment of the comparison results.

8. A method according to claim 7 wherein the unfavorable assessment of the comparison results is indicated in an audible manner to the patient having said transplanted heart.

9. A method according to claim 1 wherein only analog electrocardiac signals with a frequency signal range of 0.016 Hz to 1 KHz are supplied for conversion to the digital signals.

10. A method according to claim 1 wherein said analog to digital conversion occurs at a frequency of 1024 Hz.

11. A method according to claim 1 wherein the newly monitored differentiated signals and corresponding comparison results are periodically created.

12. A method of monitoring a body reaction against a heart transplanted therein, comprising steps of:
   detecting inside the body analog electrocardiac signals from a newly transplanted heart in the body;
   within the body converting the analog signals to digital signals;
   within the body carrying out a first differentiation of the digital signals over a continuous time period to create reference differentiated signals;
   at a later time during monitoring of the heart, again detecting within the body analog electrocardiac signals from the transplanted heart;
   within the body converting the analog signals to digital signals;
   within the body carrying out a first differentiation of the digital signals over a continuous time period to create newly monitored differentiated signals;
   within the body comparing at least with respect to amplitude the newly monitored differentiated signals with the reference differentiated signals to create comparison results;
   recording and storing within the body the comparison results; and
   using the stored comparison results for analyzing body rejection of the transplanted heart.

* * * * *